United States Patent [19]

Bornengo et al.

[11] 4,171,321

[45] Oct. 16, 1979

[54] ZINC CHLORIDE ADDUCT OF BENZYL-N,N-DI-SEC. BUTYLTHIOLCARBAMATE AND USE THEREOF AS CATALYST FOR PREPARING BENZYL-N,N-DI-SEC. BUTYL-THIOLCARBAMATE FROM CARBAMOYL CHLORIDE AND BENZYL MERCAPTAN

[75] Inventors: Mario Bornengo; Sergio Bacciarelli, both of Massa; Sergio Serdi, Milan, all of Italy

[73] Assignee: Montedison S.p.A., Milan, Italy

[21] Appl. No.: 892,399

[22] Filed: Mar. 31, 1978

[30] Foreign Application Priority Data

Apr. 1, 1977 [IT] Italy ............................... 22010 A/77

[51] Int. Cl.$^2$ ..................... C07C 155/08; C07F 3/06
[52] U.S. Cl. ............................ 260/455 A; 260/429.9
[58] Field of Search ........................ 260/429.9, 455 A

[56] References Cited

U.S. PATENT DOCUMENTS 2,983,747   5/1961   Campbell et al. ............... 260/455 A Primary Examiner—John M. Ford
Assistant Examiner—Robert C. Whittenbaugh

[57] ABSTRACT

An adduct of zinc chloride and benzyl-N,N-di-sec. butyl-thiolcarbamate, and use thereof as catalyst for preparing benzyl-N,N-di-sec.butyl-thiolcarbamate from carbamoyl chloride and benzyl mercaptan are disclosed.

10 Claims, No Drawings

ZINC CHLORIDE ADDUCT OF BENZYL-N,N-DI-SEC. BUTYLTHIOLCARBAMATE AND USE THEREOF AS CATALYST FOR PREPARING BENZYL-N,N-DI-SEC. BUTYL-THIOLCARBAMATE FROM CARBAMOYL CHLORIDE AND BENZYL MERCAPTAN

THE PRIOR ART

As is known from Italian Patent No. 907,710, benzyl-N,N-di-sec.butyl-thiolcarbamate (marketed by Montedison S.p.A. under the registered trademark "Drepamon") is a weed-killer for rice fields which exerts a trophic action on rice. As is also known from Italian Pat. No. 971,612, "Drepamon" can be synthesized from N,N-di-sec.butyl-carbamoyl chloride and benzyl mercaptan in the presence of catalytic amounts of powdered zinc, iron, tin or DeVarda alloy.

In practice, said process for synthesizing "Drepamon" has the following drawbacks:

(1) it is difficult to distribute the catalyst homogeneously in the reacting mass, which can involve sedimentation when there are marked differences between the densities of the reagents, and lead to sudden and strong exothermal phenomena which render it difficult to "drive" the reaction;

(2) the reaction rate depends on the purity and state of the catalyst surface, which strongly influences the yields, and a portion of the non-reactive catalyst remains in the reaction product, in the form of oxides, salts, etc., to pollute it, thus requiring subjecting the reaction product to difficult and expensive filtrations, centrifugings, etc.;

(3) relatively large amounts of catalyst with respect to the reagents are necessary; and (4) hydrogen is involved and is difficult to remove from the exhaust gases.

THE PRESENT INVENTION

One object of this invention is to provide a new and improved process for synthesizing "Drepamon" which does not have the disadvantages of the aforesaid known process.

This and other objects are achieved because we have found that benzyl-N,N-di-sec.butyl-thiolcarbamate ("Drepamon") binds mole to mole stoichiometrically to anhydrous zinc chloride to give, as adduct, a viscous, yellow oil which is completely soluble in "Drepamon" and in benzyl mercaptan.

The adduct has the formula

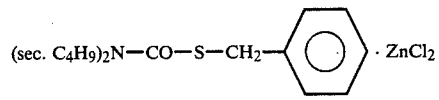

and the following characteristics:
 viscosity = 1600 poises (at 20° C.)
 density = 1.19 poises (at 20° C.)
and is decomposed by water into "Drepamon" and zinc chloride. The IR spectrum confirms the proposed formula.

The adduct can be used in the synthesis of "Drepamon" as substitute for the catalysts of Italian Pat. No. 971,612, with the following advantages:

(I) 0.03 gram-atom of the zinc contained in the adduct is used for each mole of the reagents reacted, in contrast to the 0.07 gram-atom of zinc per mole which is employed according to Italian Pat. No. 971,612;

(II) since the adduct of this invention is soluble in both "Drepamon" and benzyl mercaptan, it is homogenously distributed in the reacting mass;

(III) the reaction rate is adjustable by addition of reagents since zinc chloride impurities, if any, do not bind with the adduct;

(IV) there is no evolution of hydrogen;

(V) because the adduct (catalyst) decomposes in the presence of water to "Drepamon" and water-soluble zinc chloride, it can be readily removed by simply washing the reaction product; and (VI) the reaction starts immediately, without the 10-15 minutes induction time according to Italian Pat. No. 971,612.

In the process described in said Italian patent, it is necessary to first mix the catalyst with benzyl mercaptan and then add N,N-di-sec.butyl-carbamoyl chloride to the mixture. In the process of the present invention, it is possible to add the adduct also to N,N-di-sec.butyl-carbamoyl chloride and then add the benzyl mercaptan.

The benzyl-N,N-di-sec.butyl-thiolcarbamate/ZnCl$_2$ adduct of the invention can be easily prepared by homogeneously suspending equimolar amounts of "Drepamon" and ZnCl$_2$ in toluene, xylene or other suitable organic solvent, and then evaporating the solvent under reduced pressure.

If the adduct is used as catalyst for the synthesis of "Drepamon", it is possible to dissolve the ZnCl$_2$ in excess "Drepamon" and use the resulting solution without further purification.

The following examples are given to illustrate the invention in more detail and are not intended as limiting.

EXAMPLE 1

Preparation of the benzyl N,N-di-sec.butyl-thiolcarbamate/zinc chloride adduct.

A suspension of 49.1 g of ZnCl$_2$ in zylene (174 g) was added to 110 g of benzyl N,N-di-sec.butyl-thiolcarbamate at 94% purity, under stirring. The mixture was heated under stirring to 65° C. until complete dissolution of ZnCl$_2$.

Xylene was distilled at reduced pressure, thus obtaining 160 g of an adduct having the following characteristics:
 appearance: viscous, yellowish oil
 viscosity: 1600 poises (at 20° C.)
 density: 1.19 (at 20° C.)
 % of C found: 46.51, calculated: 46.22
 % of H found: 6.1, calculated: 6.04
 % of S found: 7.47, calculated: 7.71
 % of Zn found: 14.75, calculated: 15.72.

EXAMPLE 2

Use of the adduct for preparing "Drepamon."

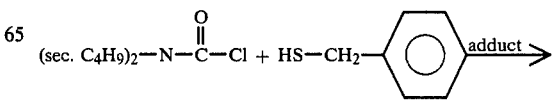

-continued

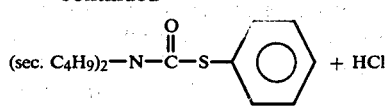 + HCl

To 287.5 g of di-sec.butyl-carbamoyl-chloride (1.5 moles) in 500 g of xylene there were added, under stirring, 18.9 g of the adduct prepared according to Example 1 (corresponding to 5.9 g of ZnCl₂). A slightly yellowish solution was obtained.

After having brought the temperature to 65° C., 187.5 g of benzyl mercaptan (1.5 moles) were added in 20 minutes.

HCl developed immediately and the reaction was completed by keeping the temperature at 65° C. for 2 hours after conclusion of the benzyl mercaptan addition. The xylene solution was washed with water and evaporated under vacuum after separation of the aqueous phase.

430 g of "Drepamon" of a purity higher than 96% were thus obtained (the yield in excess in respect of the stoichiometric amount was due to the recovery of benzyl N,N-di-sec.butyl-thiolcarbamate added in the form of adduct).

What is claimed is:

1. An adduct having the formula

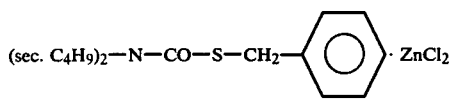

and the following characteristics:
viscosity: 1600 poises (at 20° C.)
density: 1.19 (at 20° C.).

2. The process for preparing the adduct of claim 1, which process comprises preparing a solution of $ZnCl_2$ and benzyl-N,N-di-sec.butyl-thiolcarbamate at a temperature of from room temperature to about 140° C., and filtering the solution to remove any insoluble materials.

3. The process of claim 2, in which the $ZnCl_2$ and benzyl-N,N-di-sec.butyl-thiolcarbamate are dissolved in an organic solvent.

4. The process of claim 3, in which the organic solvent is toluene.

5. The process of claim 3, in which the organic solvent is xylene.

6. The process of claim 3, in which the organic solvent is evaporated under vacuum.

7. The process for preparing benzyl-N,N-di-sec.butyl thiolcarbamate which comprises reacting N,N-di-sec.-butyl carbamoyl chloride and benzyl mercaptan in the presence of an amount of the adduct of claim 1 corresponding to 0.03 gram atoms of zinc contained in the adduct for each mole of the reactants, at 65° C. and until the reaction is complete, and then washing the reaction product with water to decompose the catalyst.

8. The process of claim 7 in which the reaction of the N,N-di-sec.butyl carbamoyl chloride and benzyl mercaptan is carried out in the presence of a solvent.

9. The process of claim 8, in which the solvent is xylene.

10. The process of claim 8, in which the solvent is toluene.

* * * * *